United States Patent [19]
Wiener

[11] Patent Number: 5,636,377
[45] Date of Patent: Jun. 10, 1997

[54] HIP PROTECTION DEVICE FOR THE ELDERLY

[75] Inventor: Stanley L. Wiener, Naperville, Ill.

[73] Assignee: Hipco, Inc., Naperville, Ill.

[21] Appl. No.: 459,349

[22] Filed: Jun. 2, 1995

Related U.S. Application Data

[63] Continuation-in-part of Ser. No. 205,286, Mar. 2, 1994, which is a continuation-in-part of Ser. No. 932,362, Aug. 19, 1992, abandoned.

[51] Int. Cl.⁶ .................... A41D 1/00; A41D 1/06; A41D 13/00; A41D 27/26
[52] U.S. Cl. .................. 2/465; 2/2.5; 2/267; 602/23
[58] Field of Search ................. 2/1, 2, 2.5, 410, 2/46, 22, 23, 24, 20, 69, 69.5, 247, 267, 268, 243.1; 602/19, 23; 450/53, 54, 55, 56, 57

[56] References Cited

U.S. PATENT DOCUMENTS

| | | | |
|---|---|---|---|
| 1,177,408 | 3/1916 | Goldman | 2/267 |
| 2,727,278 | 12/1955 | Thompson | 2/267 |
| 3,170,163 | 2/1965 | Mitchell | 2/2 |
| 3,257,666 | 6/1966 | Hoffman | 2/267 |

(List continued on next page.)

FOREIGN PATENT DOCUMENTS

| | | | |
|---|---|---|---|
| 2444428 | 8/1980 | France | 2/2.5 |
| 2527905 | 12/1983 | France | 2/69 |
| 1129430 | 5/1962 | Germany | 2/24 |
| 3638718 | 8/1987 | Germany | 2/2 |

(List continued on next page.)

OTHER PUBLICATIONS

Ross et al., "Evaluation of Two Interventions to Reduce Falls and Fall Injuries: The Challenge of Hip Pads & Individualized Elimination Rounds" *Key Aspects of Elder Care: Managing Falls Incontinence and Cognitive Impairment*, NY Springer Pub. Co., Eds Fund Sg, Tornquist Em., Champagne, MT 1992, pp. 97–103.

Wallace et al., "Iowa FICSIT Trial: The Feasibility of Elderly Wearing a Hip Joint Protective Garment to Reduce Hip Fractures", *JAGS*, Mar. 1993, vol. 41, pp. 338–340.

Lauritzen et al. "Impacts in patients with hip fractures and in vitro study of the pending effect: Introduction of a hip protector", Oct. 27/28, 1989, p. 11 (Acta Orthop Scand 1990;61 Suppl. 239).

Lauritzen et al., "Effect of external hip protectors on hip fractures", *The Lancet*, vol. 341, Jan. 3, 1993, pp. 11–13.

*Primary Examiner*—Jeanette E. Chapman
*Attorney, Agent, or Firm*—Fitch, Even, Tabin & Flannery

[57] ABSTRACT

A hip protection device for the elderly which provides protection to the trochanteric region the wearer to prevent fracture thereto upon falling from a standing position. An undergarment is provided with at least one pocket enclosing a pad, or other alternative arrangements for securing the pads to the hip regions of the garment. Each protective pad defines an open-ended channel having an elongated major axis along which it is substantially linear and a minor axis which has a generally parabolic curvature. The undergarment and pad are configured such that the pads rap around and fit snugly against the trochanteric area of the wearer's hip. Each pad has a relatively rigid, thin shield on its convex side and a relatively thin layer of resilient impact absorbing material on its concave side. Upon the wearer falling from a standing position onto their hip area, the impact force is distributed generally uniformly across the surface area of the rigid shield an then to the resilient impact absorbing material, which has sufficient resilience and thickness that greater than ninety percent of the impact force is absorbed. The undergarment and pads of the hip protection device are comfortable to wear over prolonged periods and are constructed so that they do not bulge outwardly significantly during use, making them aesthetically acceptable for users. In one embodiment for incontinent persons, a diaper is detachably engageable with the undergarment.

30 Claims, 6 Drawing Sheets

U.S. PATENT DOCUMENTS

| | | | |
|---|---|---|---|
| 3,715,733 | 2/1973 | Dubner | 2/267 |
| 3,909,847 | 10/1975 | Holt et al. | 2/2 |
| 4,441,211 | 4/1984 | Donzis | 2/2 |
| 4,462,115 | 7/1984 | Carlson et al. | 2/2 |
| 4,507,801 | 4/1985 | Kavanagh et al. | 2/2 |
| 4,573,216 | 3/1986 | Wortberg | 2/2 |
| 4,599,747 | 7/1986 | Robinson | 2/24 |
| 4,737,994 | 4/1988 | Galton | 2/2 |
| 4,761,834 | 8/1988 | Kolb | 2/2 |
| 4,805,243 | 2/1989 | Gibbens et al. | 2/247 X |
| 4,807,301 | 2/1989 | Ferber . | |
| 4,893,355 | 1/1990 | Ritter | 2/16 X |
| 4,894,867 | 1/1990 | Ceravolo et al. . | |
| 4,905,678 | 3/1990 | Cumins et al. | 602/16 |
| 4,926,883 | 5/1990 | Strock . | |
| 4,969,216 | 11/1990 | Guelli . | |
| 5,052,052 | 10/1991 | Gilford et al. | 2/267 X |
| 5,105,473 | 4/1992 | Valtakari | 2/267 X |
| 5,131,100 | 7/1992 | Atwater et al. | 2/404 X |
| 5,340,352 | 8/1994 | Nakanishi et al. | 2/267 X |
| 5,423,087 | 6/1995 | Krent et al. | 2/267 X |

FOREIGN PATENT DOCUMENTS

| | | | |
|---|---|---|---|
| 3804054A1 | 8/1989 | Germany . | |
| 3804504 | 8/1989 | Germany | 2/24 |
| 0638665 | 10/1983 | Switzerland | 2/69 |
| 2136675 | 9/1984 | United Kingdom | 2/2 |
| 2238708 | 6/1991 | United Kingdom | 2/2.5 |
| 9003126 | 4/1990 | WIPO | 2/2 |
| 9101658 | 2/1991 | WIPO | 2/2 |

HIP PROTECTION DEVICE FOR THE ELDERLY

CROSS-REFERENCE TO RELATED APPLICATIONS

This application is a continuation-in-part of U.S. patent application Ser. No. 08/205,286, filed Mar. 2, 1994, which was a continuation-in-part of U.S. patent application Ser. No. 07/932,362, filed Aug. 19, 1992 (now abandoned), both of which are hereby incorporated by reference as if fully reproduced herein.

FIELD OF THE INVENTION

The present invention pertains to a protective garment for the hip area, and more particularly, to an impact force-dissipating garment which may be worn comfortably and prevents hip injury upon falling of the user.

BACKGROUND OF THE INVENTION

It is well known to provide padding for protection of various body parts against injury due to impact to those body parts, such as football pads and other athletic apparel. However, such known padding arrangements are bulky. Since they are typically only used for short time intervals while the user is engaged in a sporting event, their bulkiness has not been of particular concern.

However, there are 200,000 to 300,000 hip fractures in the geriatric population of the United States each year. Up to 20% of such patients die within the first six months after the fracture, and 10% to 25% are permanently disabled. It is desirable to provide a padding arrangement suitable for use by elderly persons to protect their hips from injury associated with falls. Prior padding arrangements to protect the elderly hip are ineffective in dissipating and/or absorbing a sufficient portion of the impact force to the hip area associated with a fall; and have been found undesirable due to their bulkiness, discomfort over prolonged periods of use, and generally poor aesthetic appearance. Even if such pads were to provide the requisite protection of the hips in the event of a fall, many elderly persons are not aware of the beneficial attributes of hip pads. Those who are aware of the benefits afforded by hip pads often opt not to wear the pads due to the aforementioned shortcomings. Those who are aware of the benefits afforded by hip pads may choose not to purchase athletic pads due to the aforementioned shortcomings, leaving them at risk for hip injury. Accordingly, there is a need for a padding arrangement suitable for use by elderly persons which is comfortable to wear for extended periods, provides good aesthetic appearance when worn under conventional clothing, and yet which also provides sufficient protection to the hip area to prevent significant injury thereto upon a fall from a standing position. Other pads for the elderly hip tested only absorb up to 27 to 60% of the impact force. The acceptability of the looks of the padding arrangement and its ability to be worn comfortably for extended periods are critical in order to obtain actual compliance of doctors' orders that the pads be worn at all times when out of bed.

Post-menopausal women and elderly men are at particular risk for serious hip injury resulting from falls from the standing position to a hard ground surface. The trochanteric region of the femur at the hip area of elderly patients is weakened by osteoporosis and/or osteomalacia. Women lose bone mass at a rate of 1% per year after menopause until age 70, and then the rate of bone loss declines. Men have 20% more bone mass at age 40 than women, and lose bone more gradually as they age. Thus, the trochanteric regions are particularly vulnerable to fracture upon being subject to the dynamic forces associated with falling onto a non-resilient surface.

Most cases of intertrochanteric fracture involve a fall and impact to the lateral thigh and trochanteric region of the femur. Falling is common after age 70 due to neuromuscular disease, cerebrovascular disease, and cardiac disease with syncopal episodes or attacks of dizziness. Furthermore, disorders such as Parkinson's Disease, Alzheimer's Disease, and stroke are associated with high annual incidence of hip fracture.

The trochanteric region of the femur in elderly patients protrudes above surrounding atrophic gluteal and thigh muscles. This protuberant trochanteric region is a vulnerable impact site when a potential fracture victim falls on his or her side. Accordingly, it is desirable to provide a protective device which can be worn comfortably by elderly persons and which will significantly reduce the impact force to the trochanteric region of the wearer during a fall to significantly decrease the likelihood of serious hip or femur injury upon a fall from a standing position.

Several prior art devices have been developed for providing protection to the hip area, but these prior art designs suffer significant shortcomings, particularly their bulkiness. One design consists of air inflated bags inserted into laterally placed pockets of a slip or undershorts. This design requires a thick air cushion to provide the requisite impact absorption, which thickness makes the device cumbersome and uncomfortable when worn for an extended period. Also, this design requires frequent refilling of the air cushions with air. A particular shortcoming of this design, is that localized forces imparted to the pads remain localized, resulting in undesirable high localized forces imparted to the body of the wearer. Thus, with the air bag cushions, a localized impact force imparted to a peripheral portion of an airbag during a fall will not be distributed across the overall area of the cushion, as desired to reduce the fracture risk to the wearer. Additionally, the posterior placement of the lateral pockets in this design is such that a fall with the leg internally rotated will allow the direct impact of the trochanteric region of the femur with the ground surface. That is, the trochanteric region of the femur is displaced 1 to 1½ inches anteriorly when the thigh is internally rotated, resulting in uncovering of the trochanteric region and allowing for direct, inelastic impact of the trochanteric region with the ground during a fall. There is a need for a hip protection device which will provide protection to the trochanteric region regardless of the rotational position of the legs at time of impact.

Another design consists of a wrap-around padded garment that is worn over underwear and under outer clothing. Soft foam pads are provided in the hip area which do not include a hard shield associated with the foam pads. Thus, as with the aforementioned design, there is no distribution of the localized impact force and therefore localized areas of high force are imparted to the body of the wearer. This device is not designed to protect against severe osteoporosis.

Other designs having foam in the hip area have been developed, but none of these designs provide absorption of greater than 27 to 60% of the fall related impact force using the load cell accelerometer test method nor significant distribution of the localized impact force over a broader area, without adhering the hip pads directly to skin. Nor are any of the prior designs sufficiently comfortable and aesthetically pleasing to worn everyday on a regular, long term basis.

There is a need for a device for protection of the trochanteric area of the elderly which is comfortable enough to worn every day, which can be worn under the wearer's normal, unaltered clothing without creating unsightly bulges, and which can dissipate over 90% of the impact force per square inch to the trochanteric region of the femur realized from a lateral fall from a standing position.

Still further, a large number of elderly persons who may or may not require such hip protection have urinary and/or fecal incontinence. Thus, there is a need for an undergarment which is suitable for use by incontinent persons while providing, if desired, adequate hip protection.

SUMMARY OF THE INVENTION

In accordance with the present invention, a hip protection device is provided which substantially reduces the impact force to the trochanteric region of a wearer upon a fall from a standing position; yet, the device is light enough to be worn comfortably and thin enough to be aesthetically acceptable and to be worn without the necessity of larger sized clothing or wardrobe alteration.

The hip protection device constructed in accordance with the invention also provides a buttress effect to provide protection beyond the periphery of the device, so as to protect the trochanteric region of the wearer regardless of the rotational position of the leg of the wearer during a fall. Still further, the hip protection device of the present invention includes a force distributing shield to substantially reduce localized impact forces imparted to the body of the wearer.

An undergarment is provided which may have elastic pockets on either the internal surface or the external surface of the garment for receiving pads which can be positioned over the trochanteric region of the femur. The pockets may be made of slightly smaller dimensions than the pad they are designed to receive so that the pocket holds the pad snugly in place on the wearer.

The pads may define an open-ended channel having a generally elongated major axis, along which the pads are essentially linear, and a generally parabolic curve along their minor axis to comfortably fit the anteroposterior curvature of the adult hip. The pads have a rigid outer shield formed of thin layer of a rigid, shatterproof, material such as a suitable plastic, and one or more layers of shock absorbing resilient material affixed to the inside, concave surface of the rigid outer shield, such as rubber foam. Preferably the pads (including the rigid outer shell and the shock absorbing resilient material) are tapered along the outer edges to improve the aesthetic appearance when worn.

To provide a device suitable for use by incontinent persons, who may also need a hip protection device, an opening is provided in the perineal portion of the undergarment. The perineal opening is kept closed by a suitable fastener which allows easy and rapid opening of the perineal opening to allow the wearer to insert and remove loincloth type diapers or other moisture absorbing materials through the opening without the requirement of removing the garment.

Narrow complementary interengageable synthetic hook and loop strips which adhere when pressed together, such as those sold under the tradename Velcro, and hereinafter referred to as Velcro, are sewn onto the inner portion of the waistband of the undergarment in the front and rear, and positioned on the inner surface of the waist band. A narrow diaper strip, consisting of several layers of fluid absorbing material, is detachably engageable with the undergarment. Narrow strips of Velcro are sewn to the outer surface of the diaper near the front and rear edges thereof. The narrow Velcro strips on the ends of the diaper engage with respective narrow Velcro strips on the front and rear of the undergarment. Thus, the diaper may be suspended within the undergarment in a manner whereby it is easily attachable and detachable from the undergarment. In one embodiment, a foam ring is sewn between the diaper layers to relieve pressure on the skin over the sacrum. The undergarment may be provided with pockets located in the hip area which receive hip protecting pads therein, as discussed above.

In one embodiment, in which the protective pads were constructed having an overall thickness of less than 0.015 meters and weighing less than 5 ounces, the device could be concealed under ordinary clothing and worn for over 15 hours per day without discomfort or other adverse effects.

BRIEF DESCRIPTION OF THE DRAWINGS

FIGS. 24a, 24b, and 24c are views of a tapered protective pad embodying various features of the present invention.

FIGS. 25a, 25b, and 25c illustrates undershorts having interior pockets for accepting the protective pads.

DETAILED DESCRIPTION OF THE PREFERRED EMBODIMENTS

A preferred embodiment of a hip protection device is illustrated in FIGS. 1–11 and referred to generally by reference numeral 20. An undergarment in the form of undershorts 22 is provided having pockets 24 affixed to the lateral sides of the undershorts 22 for receiving respective protective pads referred to generally at 26. In accordance with the preferred embodiment of the invention, the undershorts 22 are made of a blend of approximately 92% cotton and 8% Lycra. The inherent elasticity of this material facilitates maintaining of the undershorts 22 in a stationary position so as to maintain the pockets 24, and the protective pads 26 inserted therein, in a desired protective position. The undershorts 22 include an elastic waist band 28 of approximately 1.5 inch width at the upper end thereof as with conventional undergarments, with the top of the elastic waist band 28 positioned at the iliac crest of the wearer to support the undershorts 22. The lower end of the undershorts terminates in proximity with the thighs of the wearer. Further support to the undershorts 22 is provided by the propensity of the leg components 30 of the undershorts 22 to cling to the cylindrical surface of the upper thighs of the wearer due to the elasticity of the undershorts. Still further support is provided by elastic thread 31 sewn around the lower end of each of the leg components 30.

The pockets 24 are affixed to the undershorts 22 in an area corresponding to the trochanteric region of the femur when the undershorts are pulled completely onto the wearer. In the illustrated and preferred embodiments of the invention, three pad sizes having approximately the same degree of curvature for insertion into undershorts having pockets to accommodate persons of different body sizes (see FIGS. 5–7). This leads to minimal cephalo-caudad wobble of the pad over the trochanter.

The pockets 24 are about 3 inches wide for the first small size, 4 inches wide for the second medium size and about 5 inches for the third large size. For all three sizes of the preferred embodiments, the pad is 7 inches long in the vertical direction with the pockets positioned so that the top of the pocket is 1 inch below the lower edge of the elastic waist band 28 and begins 1 inch posterior to the anterior margin of the lateral thigh and/or a vertical line projected downward from the anterior superior iliac spine. The pockets 24 have slightly smaller dimensions than the corresponding protective pads 26 that they are designed to receive. The pockets 24 are also formed of the aforementioned cotton/Lycra blend or other suitable material which allows for stretching of the pockets to accommodate a protective pad 26 of slightly larger dimensions ensuring that the pad is held snugly in the proper alignment to protect trochanteric region of the wearer. That is, the opening at the upper end of the pockets 24 stretches to allow insertion of the protective pad 26 therein and then contracts, serving as a barrier to removal of the protective pad and to hold it in the proper position despite movements of the wearer.

The positioning of the pockets 24 relative to the elastic waist band 28 is very significant. The height at which various individuals wear undershorts varies, with some individuals wearing the top of the waist band 28 one (1) inch above the iliac crest; others wearing the waist band at the iliac crest; and others position the waist band 1 inch below the iliac crest. Almost all adults have a superior trochanteric region located 3 to 4.5 inches below the iliac crest. Thus, the protective pad 26 when placed in the pocket, will cover and protect the trochanteric area regardless of which of these heights the elastic waist band is positioned on the wearer. Accordingly, when the top of the waist band 28 is worn 1 inch above the iliac crest, the upper margin of the protective pad 26 will be positioned 1.8 to 3 inches above the superior trochanteric region, and when the top of the waist band 28 is worn at the iliac crest, the upper margin of the protective pad 26 will be positioned 0.5 to 2 inches above the superior trochanteric region. At either of these positions the superior trochanteric region is covered. When the top of the waist band 28 is worn 1 inch below the iliac crest, the upper margin of the protective pad 26 will be located 0.5 inches below to 1 inch above the superior trochanteric region. The 0.5 inch of uncovering of the superior trochanteric region in this last example is compensated for by the buttress effect of the protective pad 26 which prevents direct impact of this region for 1.5 to 2 inches about the peripheral margin of the protective pad 26. The pockets 24 are sewn on the undershorts 22 with reinforced stitching to ensure that the pocket does not open or tear after a long period of carrying the device or after numerous washings.

The protective pad 26, various embodiments of which are illustrated in FIGS. 5 to 11, consists of a light, hard, shatterproof shield layer 32 such as hard plastic, metal or other suitable material, having a backing of resilient shock absorbing material 34 which may be a foam rubber product or the like. In accordance with the preferred embodiment of the invention, the plastic shield 32 is formed of acrylonitrile-butadiene-styrene (ABS) (Uniroyal Plastics, Mishawaka, Ind.) polymer which has been vacuum-molded into a generally shallow parabolic surface that approximates, rather than duplicates, the exact anteroposterior contour of the hip region of the wearer. The curvature is important in that the force per square inch imparted to the body upon impact is determined in part by the surface area of the protective shield 32. Hence, there is no super-inferior curvature to the protective pad 26, that is, no curvature along the major axis of the pad, since the human thigh is substantially flat in the vertical direction (see FIG. 11). In this preferred embodiment, the shield is approximately 0.10 to 0.125 inch thick and a layer of relatively dense polyurethane foam 36 having a thickness of approximately 0.375 to 0.4 inch is affixed with a suitable Uniroyal adhesive such as Uniroyal Adhesive M65-87 or M65-71 to the concave side of the plastic shield 32. A second layer of a relatively less dense, softer polyurethane foam 38 of approximately 0.10 to 0.125 inch thick is then adhesively affixed to the first layer 36 to form a protective pad 26 having an overall thickness of approximately 0.625 inch. The first layer of polyurethane foam 36 and the second layer of polyurethane foam 38 are coterminous with one another and coterminous with the shield 32. In one embodiment, a 0.375 to 0.4 inch layer of Ensolite foam, type HHC, and a 0.10 to 0.125 inch layer of Ensolite, type ALC or AFC produced by Uniroyal Plastics, Mishawaka, Ind., provided over 90% impact absorption during voluntary human falls from standing to a concrete surface. Alternatively, a single layer of resilient shock absorbing material (such as HHC) 34 having a thickness of about 0.5 inches may be adhesively affixed to the shield 32. In one alternate embodiment, a first layer of Poron 4701-12-20250-1604 and a second layer of Poron 4701-05-15250-1637 polyurethane foams produced by Rogers Corporation, East Woodstock, Conn., of equal thickness also provided good impact absorption. In instances where even greater protection is desired (i.e., for falls down stairs) and aesthetics and comfort are less important, the thickness of the resilient shock absorbing layer may be increased beyond 0.5 inch thick.

Based on contour mapping of the trochanteric region of the non-injured hips of actual persons who have suffered hip fractures from a fall, three different contours and sizes of ABS shields 32 with varying degrees of anteroposterior parabolic curvature have been found optimal to suffice for most hips of potential wearers. A first size of 5.5"×7" (see FIGS. 5 and 8), a second size of 4.5"×7" (see FIGS. 6 and 9), and a third size of 3.5"×7" internal diameters (see FIGS. 7 and 10) have been found to provide coverage for the injury susceptible trochanteric region of the femur when the leg is internally or externally rotated or in various degrees of hip flexion; for example, the trochanter is covered in all positions of the leg during a fall.

The 0.10–0.125 inch thickness of the plastic shield layer 32 of the protective pad 26 was arrived at by repeated testing of human volunteers falling from a standing position whereat the hips were positioned 0.3 m, 0.6 m and 0.91 m above a concrete surface with a plastic shield 32 positioned on their hip to determine the minimum thickness attainable which can survive the aforementioned falling test and sufficiently distribute the impact force; and by extensive drop weight testing. Also, the 0.50 inch foam was also arrived at by such tests to determine the minimum thickness of polymeric foam which can absorb over 90% of the impact force. In both the human fall tests and the drop weight tests, the impact force imparted to the hip was measured using piezoelectric compression accelerometers positioned on the hip surface or on the drop weight. None of the test volunteers wearing the hip pad of the present invention experienced broken bones, pain and tenderness, or other significant injuries when falling from a standing position onto a concrete surface. By contract, test volunteers falling onto unprotected hips from a height of 0.15 m experienced significant pain and tenderness.

Drop weight studies were performed using masses up to 9 kg from heights up to 36 inches. A curved wooden block was used to simulate the hip, with the piezoelectric compression accelerometers placed on the surface of the curved wooden block, and the wooden block resting on the solid ground. A platform of 9 kilograms was dropped from heights of 0.6 m and 0.9 m onto the curved surface of the wooden block. These tests were conducted both with and without the protective pad of the present invention covering the impact surface of the block. The test results showed a significant decrease in peak amplitude and an increase in the time to the peak of impact force to the block with the pad placed over the impact surface. These test results also showed a mean impact force reduction of initial impact force of greater than 90%.

In the human volunteer falls onto the hip, from heights of 0.3 m, 0.6 m and 0.91 m, piezoelectric compression accelerometer sensors were placed on the surface of the plastic shield of the protective pad and on the surface of the skin over the greater trochanter. The test results show a mean reduction in the impact force imparted to the greater trochanter of greater than 90%, and show a significant delay in force transmission through the pad, with the time from impact to the force peak being extended 0.5–1 milliseconds to up to 17 milliseconds. Also, the test results showed that the hip pads of the present invention are an effective means of preventing significant injury to the hips of persons falling from a standing position, with none of the test volunteers wearing protective padding experiencing broken bones or other significant injuries. By contrast, test volunteers falling onto unprotected hips, without the use of the hip pads, experience significant injuries.

For optimal comfort, function and aesthetic appeal, the overall thickness of the pads should be less than 0.75 inches and preferably less than 0.625 inches, while still providing sufficient impact protection.

At impact associated with a fall on the trochanteric region, the hard outer shield distributes a given local impact force, e.g., 2 to 9 square inches, over a wider area, e.g., 28 to 37 square inches (the area of the shield), thereby reducing the impact force per square inch imparted to the body of the wearer. Thereafter, the force is transmitted to the resilient material which is compressed upon impact and absorbs a substantial amount of the impact force. Transmission of the impact force through the shock absorbing resilient material is delayed for as long as 10 to 17 milliseconds, thereby lowering the impact force. Comparatively, direct impact without the shock absorbing resilient material is transmitted in 0.5 milliseconds. As a result of the above-mentioned impact dissipating effects, the pads dissipate at least 90% of the impact force per square inch resulting from such a fall.

In one embodiment of the invention which was found to provide sufficient protection of the trochanteric region of the wearer to prevent injury upon a lateral fall from a standing position, a 0.125 inch shield of hard plastic backed by 0.5 inches of rubber foam was employed. The overall thinness of the pads allows for the creation of a comfortable garment that can be worn under the wearer's normal, unaltered clothing without creating unsightly bulges; and yet, the device was still capable of dissipating 90% to 95% of the impact force of a direct lateral fall on the trochanteric region of the wearer from a standing position to a concrete surface. Thus, in effect, the device of the present invention converted a 36 inch fall to a 3 inch fall, while still being aesthetically acceptable. In tests on human subjects wearing this device, no discomfort was reported in falls on the trochanteric region from a standing position onto a concrete floor.

The elevation of the pad above the skin serves to protect the tissues in a 0.025 m to 0.05 m zone surrounding the edge of the pad from impact as well.

A protective pad 26 is inserted into each of the respective pockets 24 with the shield side 32 of the protective pad 26 facing outward, and the concave side 40 of the protective pad facing inward, toward the hip of the wearer. The slightly larger dimensions of the protective pads 26 fit snugly within the slightly smaller dimensioned pockets 24, whereby the elastic pockets 24 prevent the protective pads from shifting positions, so that the protective pads 26 are maintained directly adjacent the aforementioned trochanteric region of the hip, without significant air gaps between the body of the wearer and the pad, despite repeated movement by the wearer. This makes the hip protection device of the present invention more aesthetically acceptable than hip protection devices of prior art. Acceptability is an important factor in getting compliance of users to wear the device as instructed, and, as such, users are more likely to be protected by the hip protection device of the present invention than prior art devices simply because the users will be more likely to be wearing the present device at the time of a fall.

Figure 23:
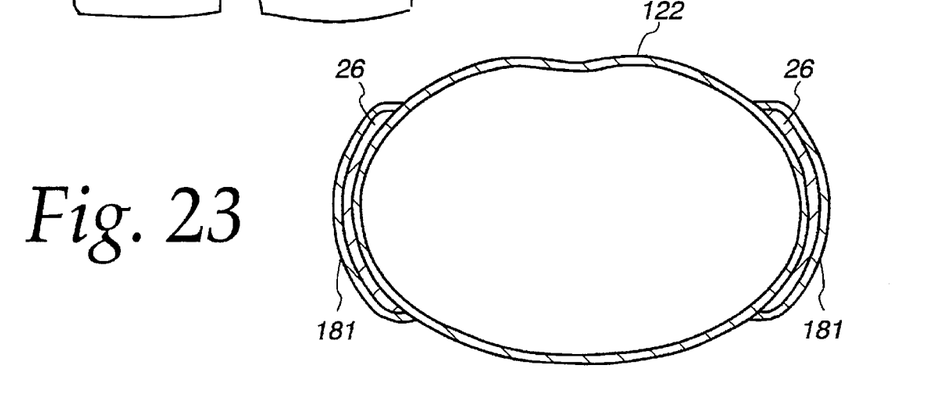
FIG. 23 is a sectional view taken along line 23—23 of FIG. 2, and is representative of the snug fit of the pads directly adjacent the hip region of the wearer.

The configuration and construction of the pads 26 of the present invention allows the pads 26 to be securely supported either completely flush or substantially flush against the hips of the wearer, as shown in FIG. 23, to minimize outward bulging of the pads which is aesthetically unacceptable for many users. More particularly, the combination of the construction of the pads 26 and the construction of the undergarment 22 combine to provide hip protection without significant outward bulging at the hips of the wearer. FIG. 23 illustrates the snugness of the hip pads against of the hips of the wearer which is attainable with the present invention.

An embodiment of the hip protection device suitable for use by incontinent patients is illustrated in FIGS. 12–15. With initial reference to FIG. 12, the undergarment comprises undershorts 122 having pockets 124 for pads 126, with the pockets 124 and pads 126 being the same as the pockets 24 and pads 26 of the preferred embodiment. The undershorts 122 are also generally the same as the undershorts 22 of the preferred embodiment, but have a pair of Velcro strips with loops 129 and 131 sewn, respectively, onto the front and rear inner surfaces of the waistband 133. A moisture absorbing diaper 135, shown in FIGS. 14 and 15, has Velcro strips with hooks 137 and 139 sewn, respectively, adjacent the front and rear ends 141 and 143 of the outer side 145 of the diaper 135. The front and rear Velcro strips 141 and 143 of the diaper 135 engage with respective front and rear Velcro strips 129 and 131 of the undershorts 122. Thereby, the diaper 135 is suspended like a hammock from the front and rear Velcro strips 129 and 131 on the inner surface of the waistband 133 of the undershorts 122 and encloses the perineum and medial upper thigh on each side of the diaper 135. To assure that the diaper 135 is centered within the undershorts 122 when attached thereto, the Velcro strips 129 and 131 are positioned on the waistband 133 of the undershorts 122 so that half of the strips are positioned on either side of the sagittal midline of the waistband 133.

The diaper 135 preferably comprises several layers of fluid absorbing cotton and/or flannel material. An annular sacral ring 147 may be sewn to the diaper 135 between the multiple layers thereof to relieve pressure on the skin over the sacrum. The sacrum ring 147 is preferably made of foam or the like and sewn 1 to 3 inches from the rear end 143 of the diaper 135. It was found that a ring 147 diameter of approximately 1.5 inches and a thickness of 0.3 inches provided good comfort.

Figures 1, 2, 3, 4, 5, 6, 7:
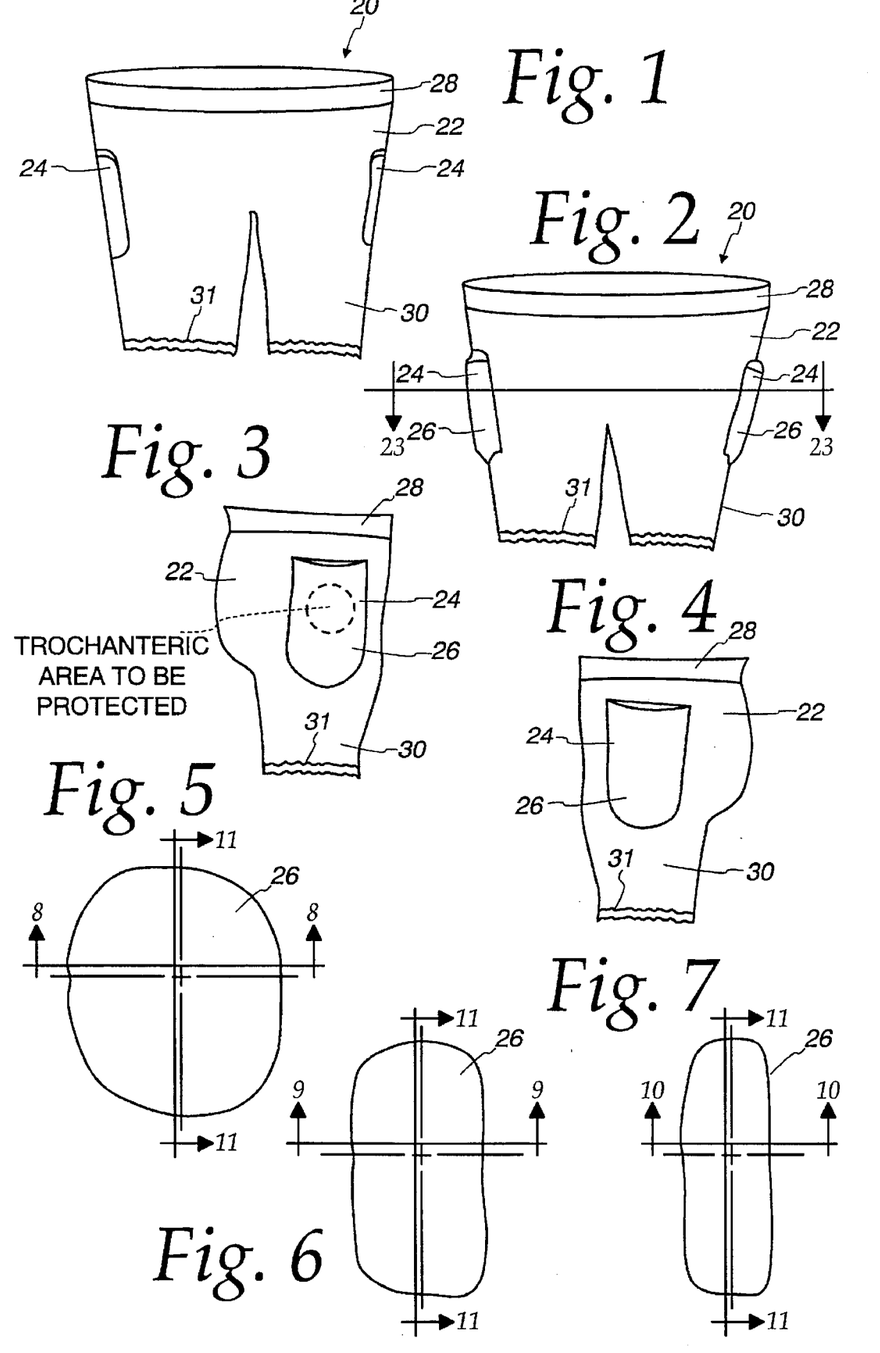
FIG. 1 is a front view of an undergarment embodying various features of the present invention.
FIG. 2 is a rear view of the undergarment of FIG. 1 with hip pads inserted in the pockets of the garment.
FIG. 3 is an elevational view of the right side of the hip protection garment shown in FIG. 1.
FIG. 4 is an elevational view of the left side of the hip protection garment shown in FIG. 1.
FIG. 5 is a plan view of a protective pad embodying various features of the present invention.
FIG. 6 is another embodiment of a protective pad.
FIG. 7 is another embodiment of a protective pad.
Figure 8:
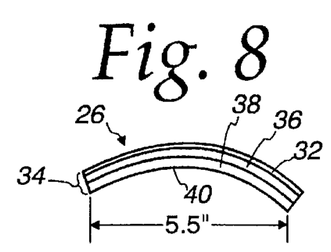
FIG. 8 is a cross section taken through line 8—8 of FIG. 5.
Figure 9:
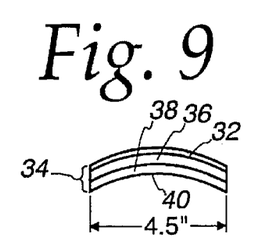
FIG. 9 is a cross section taken through line 9—9 of FIG. 6.
Figure 10:
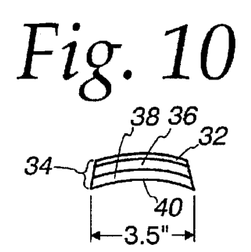
FIG. 10 is a cross section taken through line 10—10 of FIG. 7.
Figure 11:
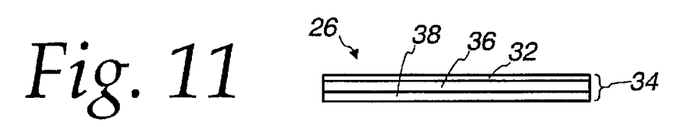
FIG. 11 is a cross section through line 11—11 of FIG. 5.
Figure 12:
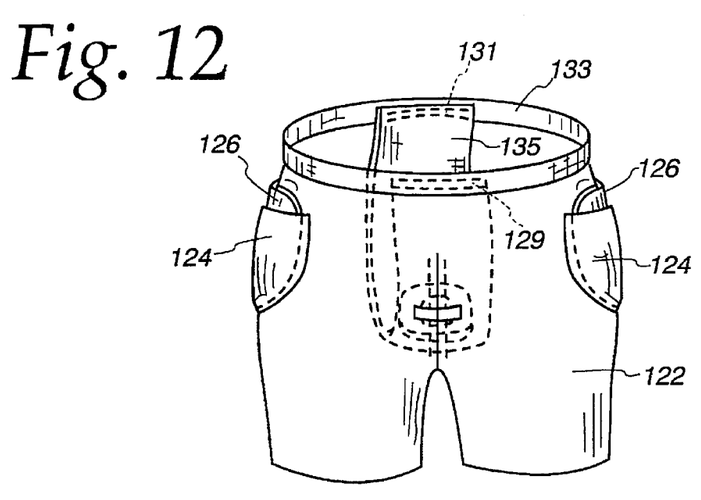
FIG. 12 is a front view of another embodiment of the hip protection device incorporating various features of the present invention, and showing a diaper fastened to an undergarment.
Figure 13:
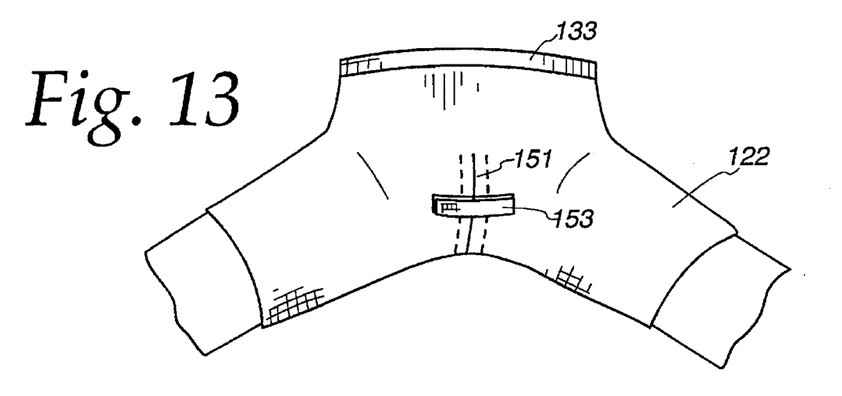
FIG. 13 is a front view of the embodiment of the hip protection device of FIG. 12, showing the perineal flap.
Figures 14, 15, 15A:
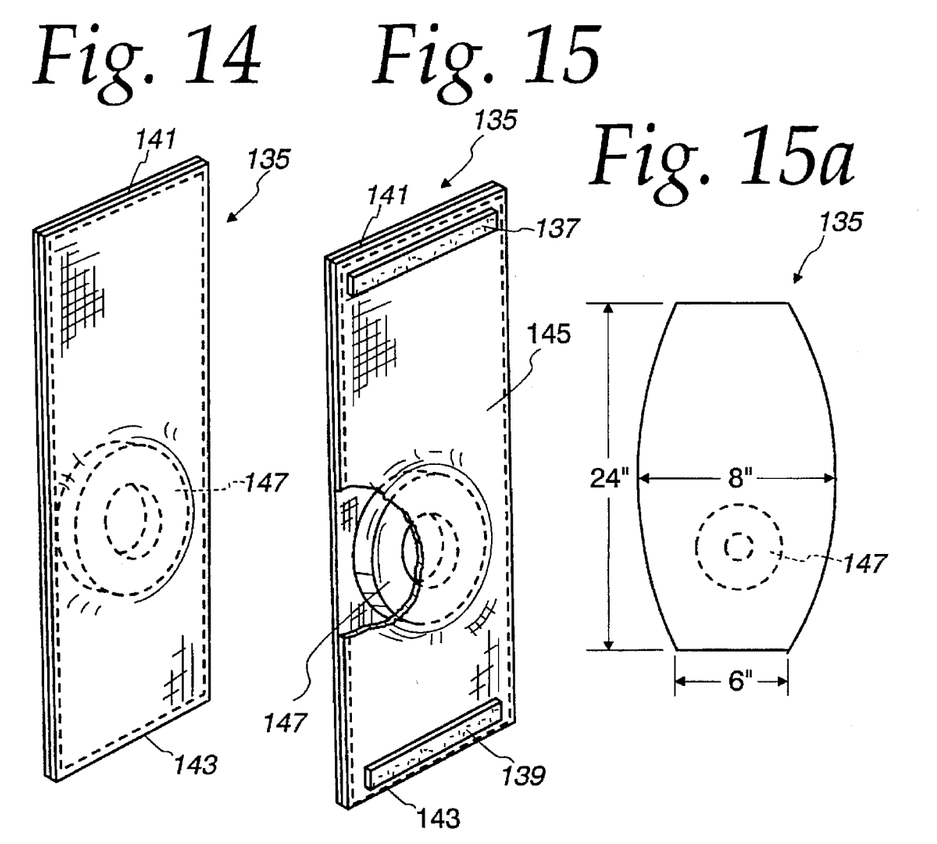
FIG. 14 is a perspective view of the inner side of the diaper of FIG. 12.
FIG. 15 is a perspective view of the outer side of the diaper of FIG. 14.
FIG. 15a is an elevational view of one embodiment of the diaper wherein the center portion is wider than the ends.

The moisture absorbing diaper is preferably narrower at its ends 141 and 143, and widens toward its center, as illustrated in FIG. 15a. It was found that a 24" long diaper 135 having a width of approximately 6 inches at its ends and a width of approximately 8 inches at its center provided good results for a wide range of different body sizes.

In accordance with one aspect of the undershorts 122, for use by incontinent persons, the undershorts 122 have a perineal opening 151 of approximately 4 or 5 inches extending along the midline seam of the undershorts 122. That is, the perineal portion of the undershorts 122 is opened over a length of about 4 or 5 inches and a 0.25 inch double thickness border is sewn around the edge of this opening for reinforcement. The perineal opening 151 is kept closed by a suitable fastener, such as a Velcro strip 153, which allows easy and rapid opening and closing of the perineal opening 151 to allow the wearer to insert and remove additional moisture absorbing materials, in addition to the diaper 135, through the opening 151 without the requirement of removing the garment.

Since the pads 26 fit snugly within their respective pockets 24 to minimize displacement of the pads 26, it may be difficult for the geriatric persons, to whom the present invention is directed, to shove the pads completely into the pockets. Accordingly, other arrangements for attaching the protective pads to undershorts are disclosed herein, and illustrated in FIGS. 16–23, which may make attachment of the protective pads to the undershorts easier for some persons.

Figure 16:
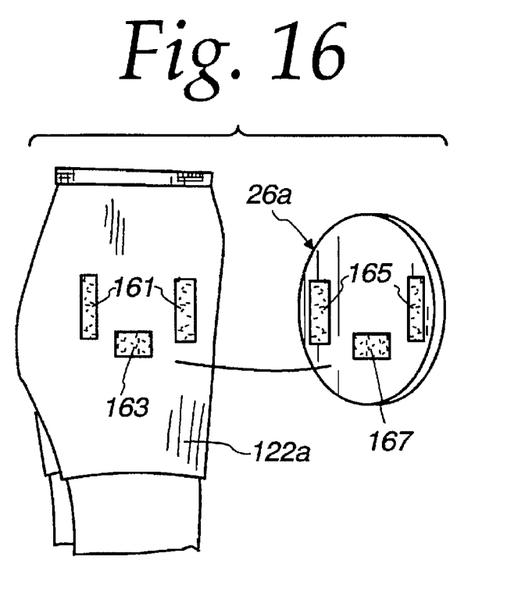
FIG. 16 is an arrangement for attaching protective pads to undershorts.
Figure 17:
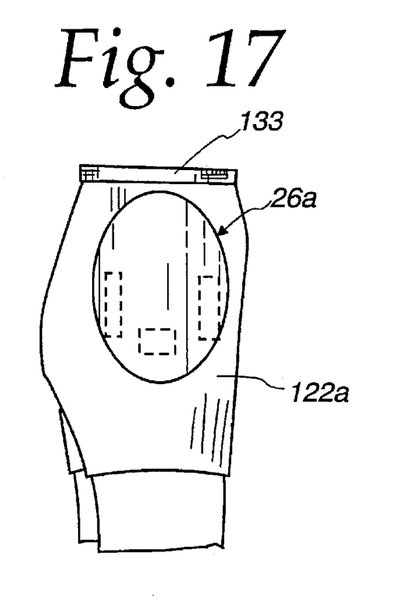
FIG. 17 is a side view of the first alternative embodiment of FIG. 16 showing the pad attached to the undershorts.

In the arrangement of FIG. 16, the undershorts 122a do not have pockets for receiving the pads 26a. Rather, two elongated strips of Velcro 161 extending vertically, and one strip of Velcro 163 extending horizontally, are bonded to the undershorts 122a, with the two vertical strips 161 extending on either side of the trochanteric hip region and the horizontal strip 163 extending below the trochanteric hip region. The pad 26a has complementary vertical strips 165 and horizontal strip 167 which engage with respective strips 161 and 163 when the pad 26a is pressed against the hip region of the undershorts 122a, to secure the pads 26a in place covering the trochanteric hip region of the wearer, as shown in FIG. 17.

Figure 18:
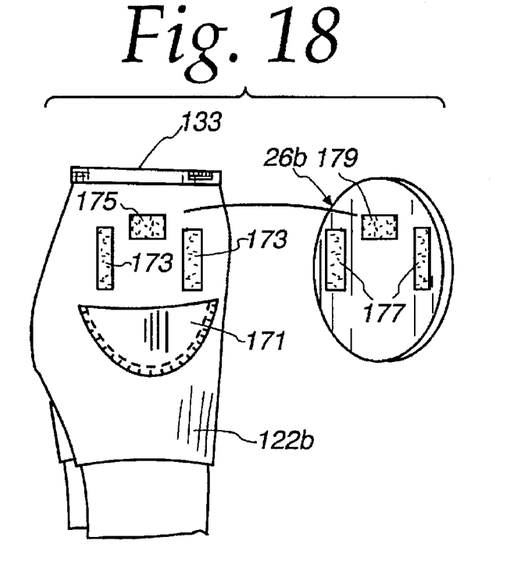
FIG. 18 is another arrangement for attaching protective pads to undershorts.

In the arrangement of FIG. 18, a shallow pocket 171 is sewn on the undershorts 122b for receiving the lower end portion of the pads 26b. The upper end portion of the pads 26b is secured to the undershorts 122b by engagement of a pair of vertically extending Velcro strips 173 and horizontally extending Velcro strip 175 sewn onto the undershorts 122b with complementary vertically extending Velcro strips 177 and horizontally extending Velcro strip 179 on the upper end of the pad 26b. The pad 26b is shown attached to the undershorts 122b in FIG. 19.

Figure 19:
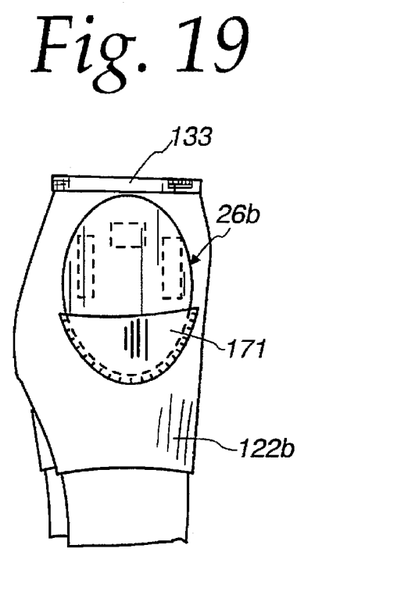
FIG. 19 is a side view of the embodiment of FIG. 18 showing the pad attached to the undershorts.
Figure 20:
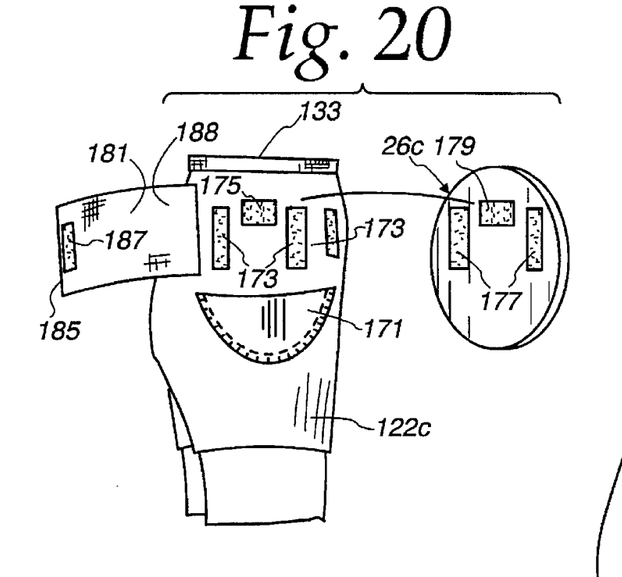
FIG. 20 is still another arrangement for attaching protective pads to undershorts.
Figure 21:
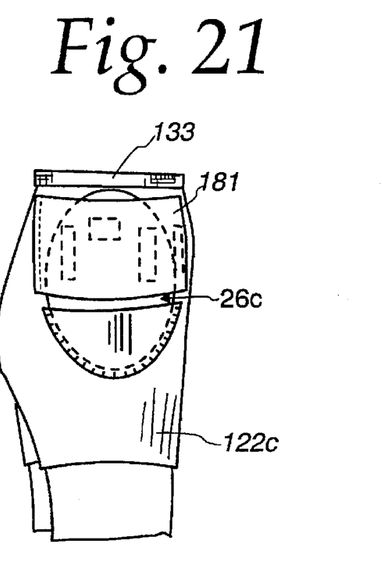
FIG. 21 is a side view of the embodiment of FIG. 20 showing the pad attached to the undershorts.
Figure 22:
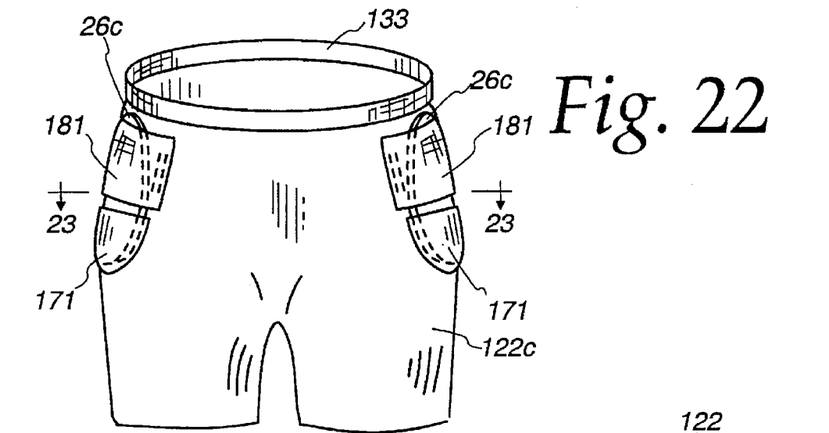
FIG. 22 is a front perspective view of the undergarment of FIGS. 20 and 21 showing a pair of pads attached to the undershorts.

In the arrangement of FIG. 20, the same shallow pocket 171 for receiving the lower end portion of the pad 26c is provided on the undershorts 122c, and the same Velcro strip arrangement on the undershorts 122c and pads 26c, as that provided on the aforementioned embodiment of FIGS. 18 and 19. Additional securing of the pads 26c in place over the trochanteric hip region of the wearer is provided by securing flaps 181, which provide additional support of the upper ends of the protective pads 26c. Securing flaps 181 have one end 183 sewn to the undershorts 122c and an opposite free end 185. A Velcro strip 187 is sewn onto the inner surfaces 188 of both of the securing flaps 181 near their free ends 185, with complementary Velcro strips 189 sewn to the undershorts 122c at locations whereat they will engage the respective Velcro strips 187 of the flaps 181 when the flaps 181 are pulled over the upper portion of the pads 26c. A pad 26c having its lower end supportably received in the shallow pocket 171 and its flap 181 pulled over the upper end of the pad 26c to secure the upper end of the pad 26c is illustrated in side view in FIG. 21, and two pads 26c attached to the undergarment 26c are illustrated in front view in FIG. 22.

Each of the embodiments of FIGS. 16–22 provide the snugness of the hip pad against the hip region of the wearer illustrated in FIG. 23. This snugness of the hip pads against the wearer minimizes outward bulging at the hip region of the wearer. The improved aesthetics and comfort over long periods of use which the hip pads of the present invention provide makes the hip pads of the present invention more acceptable to use by elderly persons, so that they are more likely to comply with doctor's demands that they be worn.

Figure 24A:
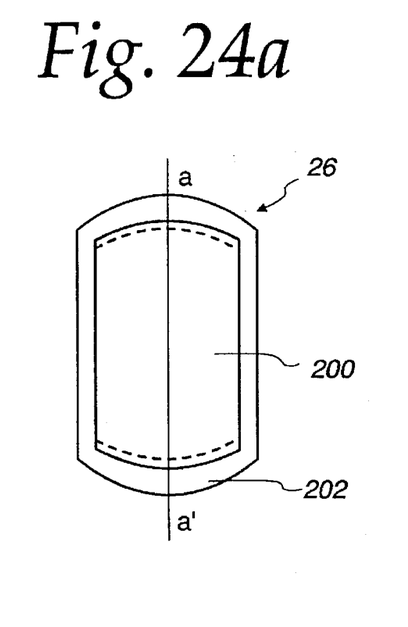
FIG. 24a is a plan view showing the surface worn away from the wearer's body.
Figure 24B:
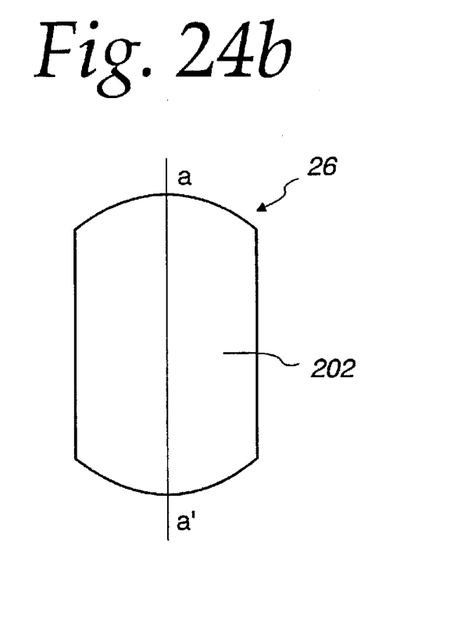
FIG. 24b is a plan view showing the surface adjacent to the wearer's body.
Figure 24C:
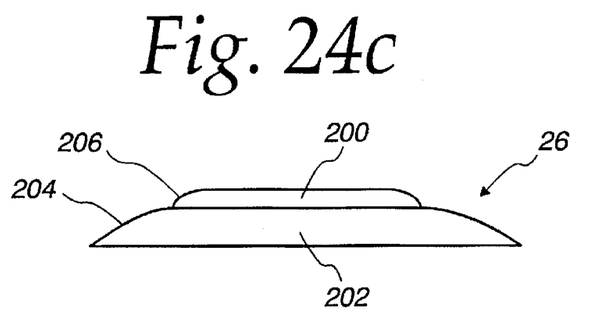
FIG. 24c is a cross-sectional view along line a–a' in FIGS. 24a and 24b.

An especially preferred embodiment of the protective pad is shown in FIG. 24. The protective pad 26 has a rigid outer surface or shell 200 (i.e., located away from the wearer's body when in use) bonded to an impact absorbing inner surface 202 as shown in FIG. 24a. FIG. 24b shows the inner surface 202 (i.e., located adjacent to the hip of the wearer) of the protective pad. Preferably, the outer edges 204 of the impact absorbing surface are tapered as shown in FIG. 24c so as to provide improved cosmetic appearance when worn. More preferably, both the outer edges 204 of the impact absorbing surface and the outer edges 206 of the rigid outer surface are tapered. Tapering the outer edges allows the protective pads to be easily "blend" in with the natural body contour and thus be less noticeable when worn. Preferably the tapers on the impact absorbing surface and the rigid outer surface form an essentially continuous, uniformly tapered line when viewed in cross-section from either side to side or top to bottom. As shown in FIG. 24a, the rigid outer surface 200 does not extend to cover the full area of the impact absorbing surface 202. This arrangement should prove more comfortable for the wearer since the edges of the rigid outer surface are effectively protected from the body by the impact absorbing surface.

Preferably, the top-to-bottom dimension of the impact absorbing surface 200 is about 7 inches and the top-to-bottom dimension of the rigid outer surface is about 5 to 5.5 inches, thus allowing about 0.75 to 1 inches non-overlap at the top and bottom (see FIG. 24a). To provide maximum protection in the case of a fall, however, it is generally preferred that this taper and non-overlap of the two surfaces occur mainly at the top and bottom of the pad. The sides of the pad, if tapering is desired, should have less taper (i.e., closer to forming a right angle between the body and the sides of the pad); moreover, there generally should be less non-overlapping of the two surface on the sides (i.e., overlapping, if any, preferably should be less than about 0.5 inches, and more preferably less than about 0.25 inches, on each side; see FIG. 24a). The tapering allows the pad to more easily blend with the natural body contours and, therefore, makes the pads less visible when worn under clothing.

Preferably the tapered rigid outer surface is ABS plastic (about 0.1 to 0.12 inches thick) and the impact absorbing surface is Ensolite (especially preferred is ALC Ensolite foam from Uniroyal Co.) which is about 0.375 to 0.40 inches thick. Preferably the ABS rigid outer portion is about 4.25 by 5.25 inches and the Ensolite foam portion is about 4.75 by 7 inches (i.e., about 0.5 inches total non-overlap side-to-side and about 1.75 inches total non-overlap top-to-bottom). Preferably the two portions are bonded together such that they are centered relative to one another as shown in FIG. 24a. Preferably the edges of both the rigid outer surface and the impact absorbing foam are tapered or beveled around the entire pad perimeter.

Figure 25A:
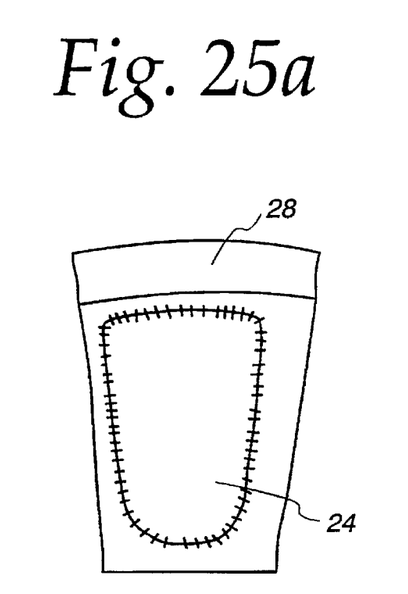
FIG. 25a shows the outside of one leg of the undershorts.
Figure 25B:
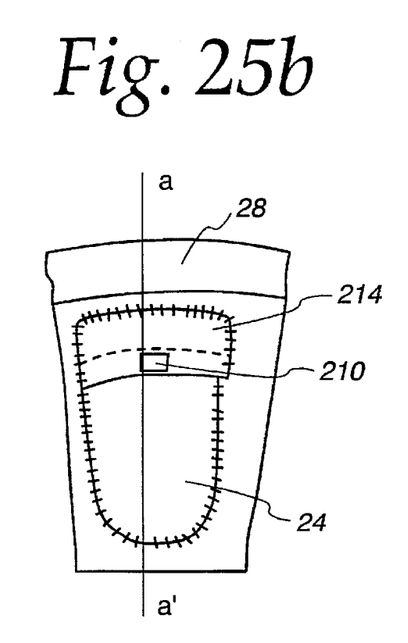
FIG. 25b shows the inside of the same leg of the undershorts.
Figure 25C:
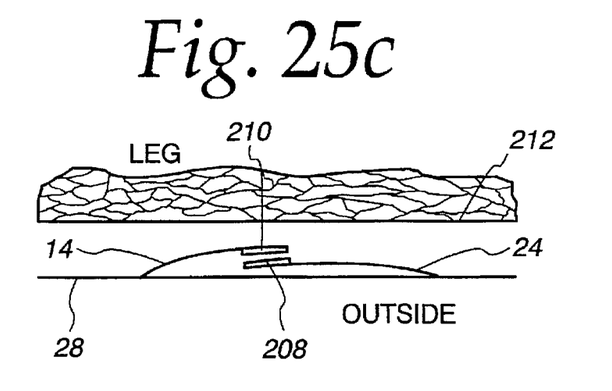
FIG. 25c is a cross-sectional view (including a portion of the leg of a wearer) along line a–a' in FIG. 25b.

FIG. 25 illustrates a garment adapted to accept the protective pads of this invention and which are especially designed for wearers who might tend to remove the pads during use. Examples of such wearers include, but are not limited to, Alzheimer patients or patients suffering from other forms of dementia who may have a tendency to remove the pads to simply "play" with them or for no reason at all. In this embodiment, the pockets for the protective pads are placed inside the garment rather than on the outside or external surface. Placement of the pockets inside the garment makes it more difficult more such patients to remove the protective pads during use. Thus, a patient suffering from dementia is more likely to have the protective pads in place in the event of a fall. At the same time, the protective pads can easily be removed in the standard manner when the garment is not being worn (e.g., for washing). FIG. 25a is a plan view of the outside leg of the garment having the pocket 24 in the interior of the garment. FIG. 25b is shows the interior of the same leg with pocket 24, Velcro fastener 210, and top pocket flap 214. The pocket 28 is located below the waist band 28 as described above. FIG. 25c shows a side view along line a–a' in FIG. 25b as well as a portion of the hip and thigh 212 of the wearer. The Velcro fastener consists of portions 210 and 208 (i.e., hooks and loops) which allows the top flap 214 to be closed and fastened to the bottom portion of pocket 24. Since both the access to the pocket 24 and the closure portions 210 and 208 are located inside the garment and are adjacent to the leg 212 during use, it is more difficult, and thus less likely, that the patient will remove the pad. The pockets placed inside the garment can be adapted to accept tapered (see FIG. 24) or non-tapered protective pads.

Although the invention has been described with regard to its preferred embodiments, which constitute the best mode presently known to the inventor, it should be understood that various changes and modifications may be made without departing from the scope of the invention which is set forth in the claims appended hereto.

What is claimed is:

1. A hip protection device for providing protection to the hip and trochanteric regions of a wearer's body and which may be worn comfortably for extended periods, said hip protective device comprising:

a garment having a waist portion and a leg portion having two legs, wherein the garment is adapted to encircle the hip and trochanteric regions of the wearer when worn, and wherein the garment, when worn, extends from the waist portion in proximity with the iliac crest of the wearer to the leg portion in proximity with the thigh regions of the wearer and each thigh of the wearer is encircled by a leg of the leg portion;

the garment having elastic means disposed in the waist portion and leg portion for elastically engaging with the wearer in proximity with the waist portion and leg portion of the garment to support the garment in a substantially stationary position on the wearer;

the garment having at least two pockets adapted to be adjacent to the hip and trochanteric regions of the wearer;

at least two separate protective pads, each protective pad adapted to be accommodated within one of the garment pockets and each protective pad having an overall thickness of less than about 0.75 inches;

each protective pad defining an open-ended channel and having an elongated major axis and a minor axis, with each protective pad being substantially linear along the elongated major axis of the protective pad and having a generally parabolic curvature along the minor axis of the protective pad corresponding to the anteroposterior contour of the hip region of the wearer, with the generally parabolic curvature defining convex and concave sides of the protective pad, and the generally parabolic curvature of the protective pad allowing substantially the entire concave side of the protective pad to reside directly adjacent to the hip region of the wearer when worn;

each protective pad comprising a force distributing shield of non-resilient material defining the convex side of the protective pad and at least one layer of resilient impact absorbing material adhered to the concave side of the force distributing shield; and each protective pad being insertable in one of the garment pockets with the force distributing shield side thereof facing outward and the concave side of the pad being substantially flush against the hip region of the wearer with the generally parabolic curvature extending in an anteroposterior direction, the resilient impact absorbing material having sufficient resilience and thickness whereby upon impact to the hip and trochanteric region of the wearer, the force of the impact is distributed over the surface area of the shield and is absorbed by the layer of impact absorbing material to the extent that at least approximately 90 percent of the impact force per square inch is dissipated to protect the hip and trochanteric region of the wearer.

2. A hip protection device in accordance with claim 1, wherein the force distributing shield comprises a layer of non-resilient plastic having a thickness of about 0.093 to 0.125 inches.

3. A hip protection device in accordance with claim 2, wherein the layer of resilient impact absorbing material comprises a foamed polymeric material having a thickness of about 0.3 to 0.5 inches.

4. A hip protection device in accordance with claim 1, wherein the layer of resilient impact absorbing material comprises a first layer of foamed polymeric material having a thickness of about 0.375 to 0.40 inches and a second layer of softer, less dense foamed polymeric material having a thickness of about 0.10 to 0.125 inches.

5. A hip protection device in accordance with claim 1, wherein the elastic means disposed in the waist portion comprises a waistband which is adapted to reside within one inch, above or below, the iliac crest of the wearer.

6. A hip protection device in accordance with claim 5, wherein the top of each pocket is about one inch below the waistband.

7. A hip protection device in accordance with claim 6, wherein the pockets begins approximately one inch posterior to the anterior margin of the lateral aspect of the thigh of the wearer.

8. A hip protection device in accordance with claim 1, wherein the protective pad provides a buttress effect to shield a region at least one inch around the periphery of the protective pad.

9. A hip protection device in accordance with claim 1, wherein the overall thickness of the protective pads is less than about 0.625 inches.

10. A hip protection device in accordance with claim 1, wherein the garment has moisture absorbing material attachable thereto.

11. A hip protection device in accordance with claim 10, wherein the dimensions of the pockets are slightly smaller than the dimensions of the protective pads to be received by the pockets, whereby the pockets may be stretched to receive the protective pads and thereafter the pockets contract around the protective pad to snugly hold the protective pads in proper relation to the hip and trochanteric region of the wearer.

12. A hip protection device in accordance with claim 1, wherein the pockets are located within the interior of the garment thereby restricting access to the pockets when the garment is worn.

13. A hip protection device in accordance with claim 12, wherein the pockets are located within the interior of the garment thereby restricting access to the pockets when the garment is worn.

14. A hip protection device in accordance with claim 1, wherein the protective pads have tapered edges to present a more pleasing appearance when the garment is worn.

15. A hip protection device in accordance with claim 12, wherein the protective pads have tapered edges to present a more pleasing appearance when the garment is worn.

16. A hip protection device in accordance with claim 13, wherein the protective pads have tapered edges to present a more pleasing appearance when the garment is worn.

17. A hip protection device which provides protection to the trochanteric region of the body of a wearer and which may be worn comfortably over extended periods, said hip protective device comprising:

a garment adapted to encircle the wearer and extending from an upper end in proximity with the iliac crest of the wearer to a lower end in proximity with the thigh region of the wearer;

the garment having elastic means disposed therein for elastically engaging with the wearer in proximity with the upper and lower ends of the garment to support the garment in a substantially stationary position on the wearer;

at least two protective pads adapted to be accommodated at the trochanteric regions of the body of the wearer, wherein each protective pad has an overall thickness of less than about 0.75 inches;

the garment and protective pads having engagement means for engagement of the protective pads to the garment at the trochanteric regions of the body of the wearer when the garment is on the wearer;

the protective pads defining an open-ended channel and having an elongated major axis and a minor axis, with the protective pads being substantially linear along the elongated major axis of the protective pads and having a generally parabolic curvature along the minor axis of the protective pads corresponding to the anteroposterior contour of the hip region of the wearer, with the curvature defining convex and concave sides of the protective pads, and the curvature of the protective pads allowing substantially the entire concave side of the protective pads to reside directly adjacent the wearer during use;

each protective pad comprising a force distributing shield of non-resilient material defining the convex side of the protective pad, with at least one layer of resilient impact absorbing material adhered to the concave side of the force distributing shield; and each protective pad being engaged by one of the pad engaging means of the garment, with the force distributing shield side of the protective pad facing outwardly and the concave side of the protective pad being substantially flush against the hip region of the wearer with the parabolic curvature of the protective pad extending in an anteroposterior direction, the resilient impact absorbing material having sufficient resilience and thickness whereby upon impact to the trochanteric region of the wearer, the force of the impact is distributed over the surface area of the shield and is absorbed by the layer of impact absorbing material to the extent that at least approximately 90 percent of the impact force per square inch is dissipated to protect the trochanteric region.

18. A hip protection device in accordance with claim 17, wherein the engagement means comprises pockets on the garment proportioned for engageably receiving one protective pad therein.

19. A hip protective device in accordance with claim 18, wherein the pockets are located within the interior of the garment thereby restricting access to the pockets when the garment is worn.

20. A hip protective device in accordance with claim 19, wherein the edges of the protective pads are tapered to present a more pleasing appearance when the garment is worn.

21. A hip protection device in accordance with claim 17, wherein the engagement means comprises narrow complementary interengageable synthetic hook and loop strips on the protection pad and the garment which adhere when pressed together.

22. A hip protection device in accordance with claim 21 wherein the engagement means further comprises a shortened lower pocket on the garment for insertion of the lower portion of the protective pad.

23. A hip protection device in accordance with claim 22 wherein the engagement means further comprises a flap having one end affixed to the garment and an opposite free end, the flap being adapted for overlapping the upper portion of the protective pad with the lower portion of the protective pad being received in the shortened lower pocket, and with the free end of the flap having means for engaging with the garment when the flap is positioned over the upper portion of the protective pad to maintain the flap in engagement over the upper portion of the protective pad.

24. A hip protection device in accordance with claim 17, wherein the garment has a front end, a rear end, and a crotch region, and the hip protection device further comprises:

an elongated strip of moisture absorbing material having opposite ends, with first engaging means adjacent each of the opposite ends;

the front and rear ends of the garment each having second engaging means adjacent the upper end of the garment for manually detachable engagement with respective first engaging means of the absorbing material; and the strip of moisture absorbing material being suspended within the garment in spaced relation from the crotch region of the undergarment upon engagement of the moisture absorbing strip with the garment.

25. A hip protection pad for residing within a pocket of a garment and being positioned at the trochanteric region of a wearer, when the garment is worn, to provide protection to the trochanteric region of the wearer, the hip protection pad comprising:

a force distributing shield of non-resilient material having a thickness of about 0.093 to 0.125 inches;

the force distributing shield defining an open-ended channel having a generally elongated major axis and a parabolic minor axis, and being substantially linear along the generally elongated major axis of the shield, and having a generally curvature along the minor axis of the shield corresponding to the anteroposterior contour of the hip region of the wearer, the generally parabolic curvature defining convex and concave sides of the shield;

a layer of resilient impact absorbing material adhered to the concave side of the shield and having a thickness of about 0.3 to 0.5 inches;

the protection pad being receivable in the pocket with the shield facing outward and the generally parabolic curvature extending in an anteroposterior direction and the protective pad having an overall thickness of less than about 0.75 inches, whereby upon localized impact to the protective pad, the localized impact force is distributed over the surface area of the shield and is absorbed by the layer of impact absorbing material to the extent that at least about 90 percent of the impact force per square inch is dissipated to provide protection to the trochanteric region of the wearer.

26. A hip protection pad in accordance with claim 25, wherein the layer of resilient impact absorbing material comprises a first layer of foamed polymeric material having a thickness of about 0.25 to 0.40 inch and a second layer of softer, less dense foamed polymeric material having a thickness of about 0.10 to 0.25 inches.

27. A hip protection device for a person with incontinence which provides protection to the trochanteric region of the body of the person and provides absorption of bodily waste, the hip protective device comprising:

a garment adapted to encircle the person, extending from an upper hip engaging portion in proximity with the iliac crest of the person to a lower thigh engaging portion in proximity with the thigh region of the person;

the garment having elastic means disposed therein for elastically engaging with the person in proximity with the upper and lower portions of the garment to support the garment in a substantially stationary position on the person;

at least two protective pads adapted to be accommodated at the trochanteric regions of the person when wearing the garment;

each protective pad defining an open-ended channel and having an elongated major axis and a minor axis, with the protective pad being substantially linear along the elongated major axis of the protective pad and having a generally parabolic curvature along the minor axis of the protective pad corresponding to the anteroposterior contour of the hip region of the wearer, with the curvature defining convex and concave sides of the protective pad, and the curvature of the protective pad allowing substantially the entire concave side of the pad to reside directly adjacent the person when the garment is worn;

each protective pad comprising a force distributing shield of non-resilient material defining the convex side of the protective pad, and at least one layer of resilient impact absorbing material adhered to the concave side of the force distributing shield;

wherein each protective pad has an overall thickness of less than about 0.75 inches;

attachment means for attaching each protective pad with the garment at respective positions corresponding to the trochanteric regions of the person with the force distributing shield side thereof facing outward and the concave side of the pad being substantially flush against the trochanteric region of the person, the resilient impact absorbing material having sufficient resilience and thickness whereby upon impact to the trochanteric region of the wearer, the force of the impact is distributed over the surface area of the shield and is absorbed by the layer of impact absorbing material to the extent that at least approximately 90 percent of the impact force per square inch is dissipated to protect the trochanteric regions of the wearer;

the hip engaging portion of the garment having a front end and rear end;

an elongated strip of moisture absorbing material having opposite ends, with garment engaging means adjacent to each of the ends; and the front and rear ends of the hip engaging portion of the garment each having diaper engaging means;

the strip of moisture absorbing material being engageable with the garment by engagement of the garment engaging means of the strip of moisture absorbing material with the diaper engaging means of the garment.

28. A hip protection device in accordance with claim 27, wherein the attachment means comprises shallow pockets sewn to the undergarment at the regions corresponding to the trochanteric regions of the person, with the shallow pockets receiving the lower ends of the protective pads.

29. A hip protection device in accordance with claim 28, wherein the attachment means comprises flaps sewn to the garment having one of their ends sewn to the garment at the regions corresponding to the trochanteric regions of the person with the other end of the respective flaps being a free end, the respective flaps being moveable from a first position spaced from the protective pads to expose the protective pads for insertion and removal from their respective shallow pockets, and a second position in which the flap extends across the upper portions of the respective protective pads and the free ends of the flaps engage with the garment to secure the protective pads in a stationary position.

30. A hip protection device in accordance with claim 27, wherein the attachment means comprises pockets for receiving the protective pads, wherein the pockets are located inside the garment thereby restricting access to the protective pads when the garment is worn, and wherein the protection pads have tapered edges.

\* \* \* \* \*

UNITED STATES PATENT AND TRADEMARK OFFICE
CERTIFICATE OF CORRECTION

PATENT NO. : 5,636,377
DATED : June 10, 1997
INVENTOR(S) : Stanley L. Wiener

It is certified that error appears in the above-indentified patent and that said Letters Patent is hereby corrected as shown below:

Column 13, line 39, change "pockets begins" to --pockets begin--.

Column 15, line 53, after "generally" insert --parabolic--.

Signed and Sealed this

Eighth Day of September, 1998

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,636,377
DATED : June 10, 1997
INVENTOR(S) : Stanley L. Wiener It is certified that error appears in the above-identified patent and that said Letters Patent is hereby corrected as shown below:

Column 13,
Line 64, change "12" to -- 11 --.

Signed and Sealed this

Twenty-eighth Day of February, 2006

JON W. DUDAS
*Director of the United States Patent and Trademark Office*